United States Patent

Father

[11] Patent Number: 5,331,983
[45] Date of Patent: Jul. 26, 1994

[54] COMBINED TOOTHBRUSH AND DENTAL FLOSSING TOOL

[76] Inventor: Richard M. Father, P.O. Box 33918, Seattle, Wash. 98133

[21] Appl. No.: 33,579

[22] Filed: Mar. 18, 1993

[51] Int. Cl.⁵ .............................................. A45D 44/18
[52] U.S. Cl. ..................................... 132/309; 132/310
[58] Field of Search ............... 132/308, 309, 310, 322, 132/323, 326, 327; 15/167.1, 167.2; 128/62 A

[56] References Cited

U.S. PATENT DOCUMENTS

| | | | |
|---|---|---|---|
| 1,852,480 | 4/1932 | Ruetz | 132/309 |
| 2,754,833 | 7/1956 | Vecchio | 132/309 |
| 2,798,241 | 7/1957 | Cohen | 132/309 |
| 2,807,820 | 10/1957 | Dinhoffer | 15/167.1 |
| 3,106,216 | 10/1963 | Kirby | 132/326 |
| 3,230,562 | 1/1966 | Birch | 128/62 A |
| 3,953,907 | 5/1976 | Froidevaux | 15/167.2 |
| 3,978,852 | 9/1976 | Annoni | 15/167.1 |
| 4,031,908 | 6/1977 | Ting | 132/322 |
| 5,094,256 | 3/1992 | Barth | 132/323 |
| 5,137,039 | 8/1992 | Klinkhammer | 132/308 |

FOREIGN PATENT DOCUMENTS

| | | | |
|---|---|---|---|
| 8807354 | 10/1988 | PCT Int'l Appl. | 132/323 |
| 2169499 | 7/1986 | United Kingdom | 15/167.2 |

*Primary Examiner*—Robert P. Swiatek
*Assistant Examiner*—Frank A. LaViola

[57] ABSTRACT

Two joinable tooth brushes, each having a slot extending approximately to the center of the bristle head, co-operate to form a double brush in a Y shaped handle and permitting a length of dental floss to be strung through the brushes and across the Y. The invention is particularly suited for concurrent cleaning interdental surfaces, the V shaped entrances thereto, and the proximal gum lines.

7 Claims, 2 Drawing Sheets

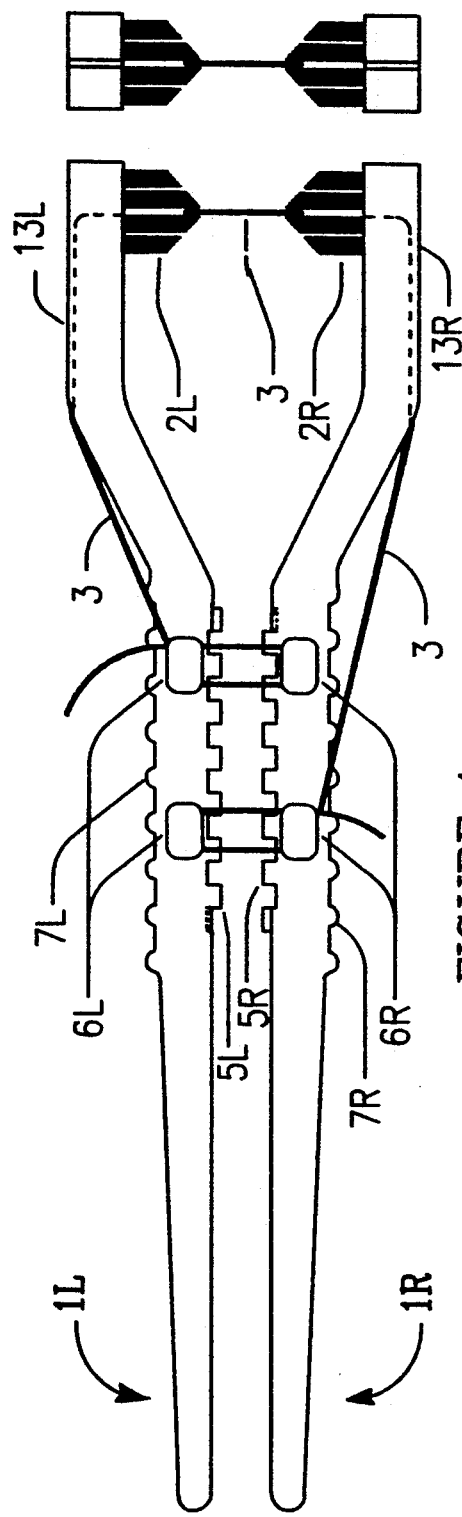
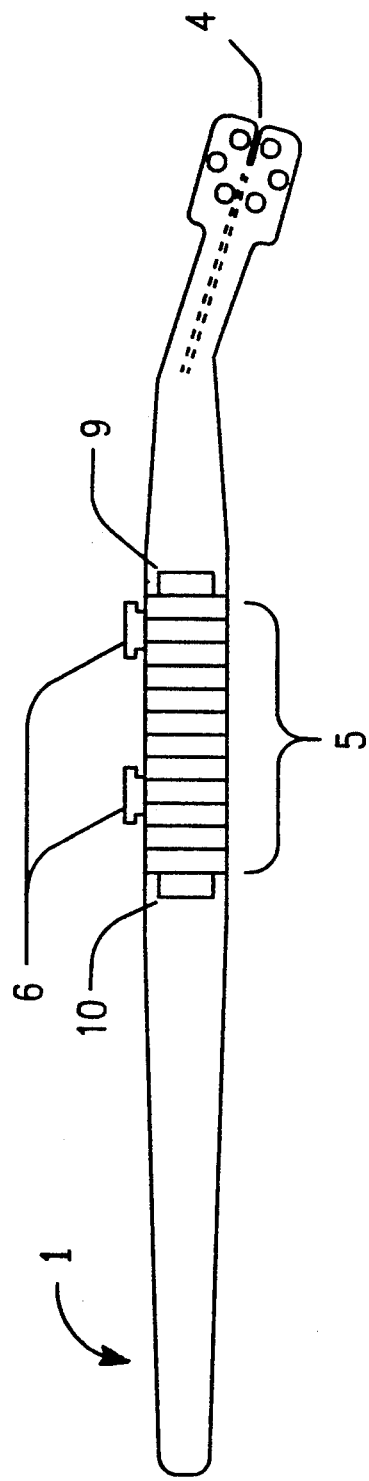
FIGURE 1
FIGURE 2

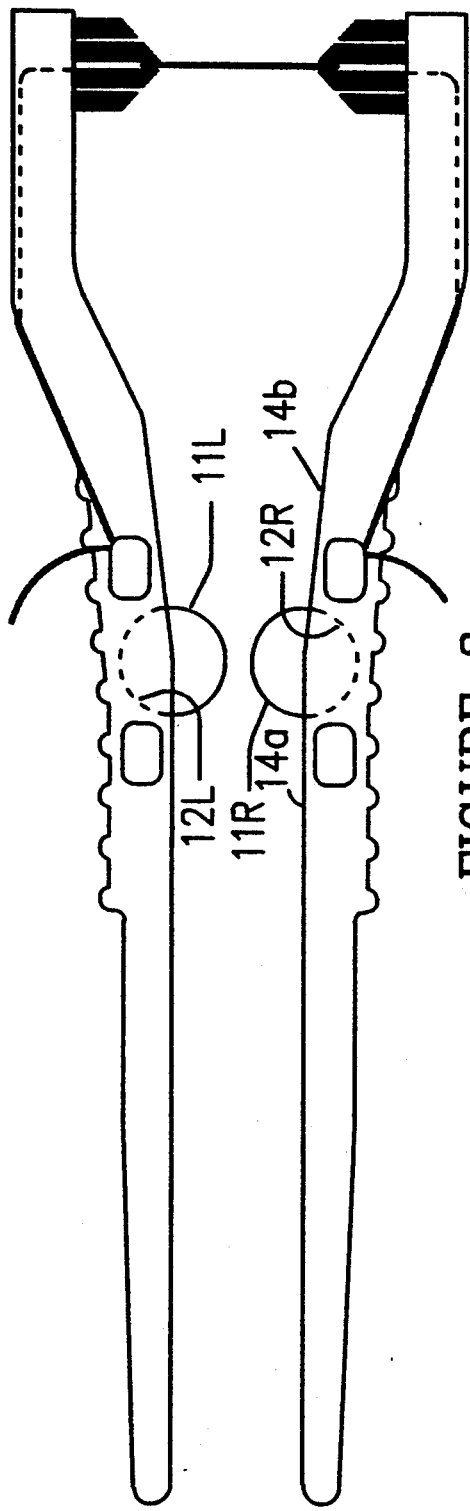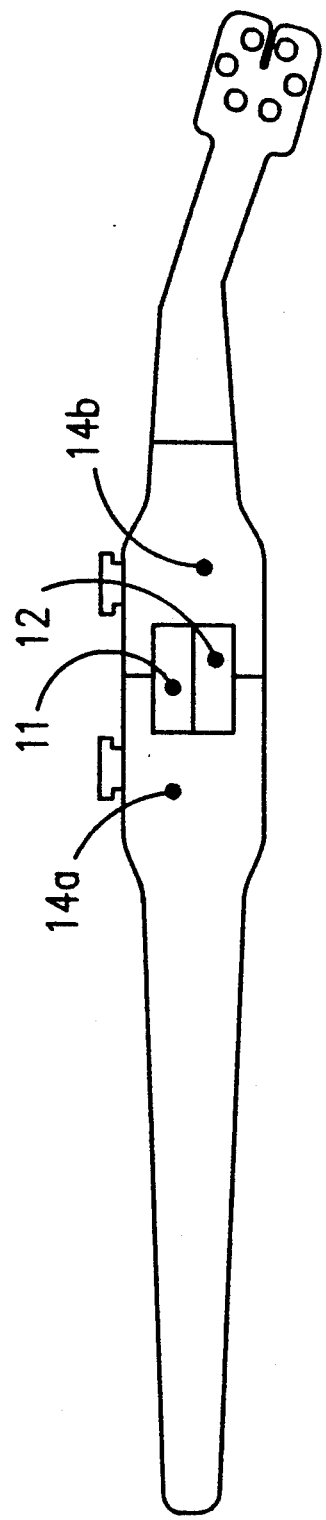

COMBINED TOOTHBRUSH AND DENTAL FLOSSING TOOL

REFERENCES

U.S. Pat. No. 4,498,209. Twin Dental Brush. Leslie Weiss. Feb. 12, 1985.

U.S. Pat. No. 4,004,597. Means for Supporting a Strip of Length of Dental Floss in Tensioned and Taut Condition for Ready use. Sam Kupperman, Dennis Kupperman. Jan. 15, 1977.

U.S. Pat. No. 5,029,593. Device for Cleaning of the Teeth. Paavo Huttunen. Jul. 9, 1991.

U.S. Pat. No. 5,094,256. Dental Cleansing Device and Interdental Floss for such a Device. Frederic Barth. Mar. 10, 1992.

BACKGROUND OF THE INVENTION

1. Field of the Invention.

The present invention relates to a double headed brush coupled with a dental floss holder to permit simultaneous brushing of both sides of the teeth while flossing the interdental surfaces.

2. Description of Prior Art

The common method of cleaning teeth is to pass a single brush over each accessible surface followed by passing a specially prepared string between the teeth to clean the interdental surfaces un-reachable by a brush. Many people then re-brush to ensure that the interdental particles are removed from the zone to the teeth. The present invention permits a person to perform all three functions with one implement, and approximately simultaneously. It also encourages the equivalent of re-brushing after flossing.

Common brush configurations are designed such that they operate with preference to cleaning the outer flat surfaces of the teeth. The curved surfaces connecting the outer surfaces and the interdental surfaces are cleaned, but only because the brushing operation forces some of the bristles into the entrances slots.

Multiple brush assemblies and specially shaped brushes have been invented to simultaneously brush cheek and lingual surfaces of teeth. U.S. Pat. Nos. 4,498,209, 5,094,256 and others have examples of dual brush assemblies. Many devices have been invented to more easily utilize dental floss. These usually take either of two shapes, a forked handle or a bow handle, with the dental floss strung between co-operating floss guides. Most of these also contain a holding chamber for a spool of common floss. A few flossing aids have separate handles, which are basically finger analogs, manipulated either by both hands or one hand chopstick style. U.S. Pat. No. 5,094,256, is one of many examples of a fork type flosser. Integral floss spool holders are generally rejected because of the probability of contamination of the floss supply in the spool during normal use.

Barth, U.S. Pat. No. 5,094,256, is the only prior art found that combines tooth brushes and dental floss for simultaneous use. Barth's floss is strung along side and a little apart from the brushes. The position taught by Barth interferes with both the co-operation of the brush and floss to clean teeth better than the prior art. The position also interferes with proper application of the brushes to both adjacent teeth and associated gum lines.

Barth's disclosure teaches floss threaded through holes in a forked handle. Barth recites difficulty with threading floss through holes, particular in the presence of water. Barth provides a solution to the threading problem by adding a new structural element in the form of fastening a length of floss to a needle like rod for inserting through the holes. This solution also teaches away from any invention designed for simultaneous use of floss and brushes, because, as taught, it precludes simultaneous use of his brushes and floss.

The present invention overcomes these objections by providing floss holding slot terminating near the center of the bristle bunches at the working head of the tooth brush. With this new configuration, threading is easily accomplished wet or dry and the brushes can work all around the strand of floss.

SUMMARY OF INVENTION

This invention relates to a toothbrush assembly designed to emphasize the cleaning of interdental surfaces and the curved surfaces leading to the opposing faces of two adjacent teeth. The invention consists of two brushes which may be used individually or joined together as a double brush and dental floss holder. Common tooth brushes are basically straight handled. The small bends in the vicinity of the brush head are to adjust the positions of the brush. This invention also has bends in the handles, but they are to set the angle of the brush, to set either relative position when the two handles are joined, and to form a fork shape, between which a length of dental floss is Conventional manufacture of a toothbrush is to set the brushes in bundles. Several bundles comprising the brush bristle structure. Each bundle is often cut to have a conical end or any other shape conducive to establishing the overall shape of the brush. In this invention, the bristles are cut to form a cone shape or alternatively a wedge or roof shape which is specifically intended to reach as far as possible into the wedge or V shaped entrance between adjacent teeth to emphasize cleaning of these hard to clean tooth surfaces. The string of dental floss also confines the zone of motion of the brush to the critical areas of the tooth surfaces and gums relative to the conjunctive faces of the dental arch. Thus, the cleaning action emphasizes and enhances the operation of cleaning the most difficult and also critical areas of teeth.

FIG. 1 illustrates this invention in two views. Brush bundles are shown in a circular pattern, but may equally be set into rows.

Accordingly, it is an objective of the invention to improve net quality of dental hygiene using flossing and brushing techniques.

Another objective of this invention is to provide a brush shaped specifically to enhance the cleaning of curved tooth surfaces of the opposing interdental surfaces, and the concurrent massage of the associated gum line.

Another objective of this invention is to permit easy handling of dental floss and simultaneously perform brushing operations of the adjacent surfaces.

Another objective of this invention is to permit several options in the use of the invention, such as an individual brush, single brush with dental floss, or as a finger analog for manipulating dental floss.

Other objects and advantages of the invention will become apparent from the specifications and drawings.

BRIEF DESCRIPTION OF THE FIGURES

FIG. 1 is an exploded view of the flossing/brushing tool illustrating its assembly and essential parts.

FIG. 2 is a detail of one handle piece. The other handle piece is a mirror image, otherwise identical.

FIGS. 3 and 4 are of an embodiment with variable tensioning means utilizing a hinge-like mechanism.

DETAILED DESCRIPTION OF PREFERRED EMBODIMENT

In the preferred embodiment, two individual brushes 1L and 1R are designed as a set of left and right parts with means 5, 9, and 10 to join them together. Thus, forming a double brush and floss holding yoke, as a tool for simultaneously brushing and flossing teeth. The bristles 2L and 2R of the brushes are shaped to specifically clean the curved surfaces between the teeth.

In the embodiment illustrated in FIGS. 1 and 2, the first fixing means is a set of rises and valleys 5 traversing the width of the brush handle and co-operating interdigitally with matching rises and valleys of the opposite handle, and backed by mortice and tenons, 9 and 10, at each end of the rises and valley pattern. Additional securing of the two handle pieces is provided by winding the floss around both of co-operating bollards 6L and 6R, located on each handle piece. Other shapes within the general concept describe will cooperate with equal results to fix the handles together in proper relative position. The bends or angles in the handles are of proper degree to place the distal end of the tool in the optimum position for the operation of flossing and brushing teeth. The angles are also chosen to perform a guide function for the floss traversing the distance among the handles between the distal slots and the floss securing bollards 6.

Gripping surfaces 7L and 7R are equipped with roughness or shape to enhance friction between the operating hand and the handles. The specific shape is not critical and may include decorative pattern.

Brushes 2 cooperate with the various angles of the shape of the handles to position said brushes opposite each other and separated ends by the approximate thickness of a molar tooth.

In operation, the handles are assembled and the floss threaded through the approximate center of the brush. In use, the floss is inserted between the teeth and brush moved over the teeth. The floss restricts the movement to the area spanning two teeth and the brush head with a conical or wedge shape is particularly suited to clean the between-teeth groove and simultaneously massage the most critical portion of the gum line. The floss is then moved to the next tooth pair and the process repeated. From this description, it is evident that the present invention virtually mandates that careful attention be paid to the most critical and most often neglected surfaces of the tooth arch.

A second embodiment is described wherein the joining means is a hinge-like structure but without a hinge pin. The hinging function is provided by the cylinders 11L and 11R rotating in their respective cylindrical slots, 12L and 12R, as if pinned, yet the assembly may be disassembled simply by separating the handles. The hinge function of this embodiment permits the tool to adjust the floss tension by rocking the handle causing rotation of the hinge means and consequent movement of the brushes toward and away from each other, which also pulls the floss strung between. Rocking option is limited by the angle between the handle surfaces, 14a and 14b, before and after the axis of the cylinders.

The invention may be used in other configurations, mainly, without floss, individually, as a single brush with floss in conjunction with a finger as the opposite floss holder, or as a finger extension or analog for conventional flossing of specific problem areas. A worn brush instead of being discarded, may have the bristles cut away and used as a flosser only.

Of course, the present invention is not intended to be restricted to any particular form or arrangement, or any specific embodiment disclosed herein, or any specific use. Since the same may be modified in various particulars or relations without departing from the spirit or scope of the claimed invention shown hereinafter. The description of the apparatus is intended only for illustration and for disclosure of an operative embodiment and not to show all of the various forms of modification in which the invention might be embodied or operated.

The invention has been described in considerable detail in order to comply with the patent laws by providing a full public disclosure of at least one of its forms. However, such detailed description is not intended in any way to limit the broad features or principles of the invention, or the scope of patent monopoly to be granted.

I claim:

1. A dental hygiene tool combining brushing and flossing comprising:
    a first handle means;
    a second handle means;
    a first bristle brush means;
    a second bristle brush means;
    each said first and second bristle brush means defining a periphery;
    slot means terminating within said first and second bristle brush means;
    a length of dental floss;
    an attachment means for securing an end of said dental floss to said first and second handle means;
    said first and second handle means being joined together to form a Y shape, said Y shape having distal ends and supporting said first and second bristle brush means at said distal ends of said Y shape and said slot means terminating within the periphery of each said bristle brush means;
    whereby said slot means co-operate to support said length of dental floss strung between said first and second bristle brush means.

2. The dental hygiene tool of claim 1 wherein said attachment means comprises at least one bollard.

3. The dental hygiene tool of claim 1 wherein said first and second bristle brush means each have a cone shaped working face.

4. A forked type dental hygiene tool combining brushing and flossing comprising:
    first and second brush means each comprising a handle means having a gripping portion attached to a first offset portion and second offset portion attached to the first offset portion;
    a bristle brush means perpendicularly attached to each of said second offset portions of said handle means;
    fixing means for fixing relative positions of said first and second brush means when joined;
    a length of dental floss;
    a slot means for guiding support of said length of dental floss;
    an attachment means for securing ends of said length of dental floss to said handle means;

said slot means extending from a distal end of said handle means to approximately a center area of said bristle brush means and;

wherein said first and second brush means are mirror images of each other and are joined by said fixing means to form a Y shaped yolk having forked portions with said bristle brush means oriented inwardly within the forked portion of said Y shaped yoke and said slot means guiding and supporting said length of dental floss strung between the bristle brush means.

5. The forked type dental hygiene tool of claim 4 wherein said attachment means comprises at least one bollard.

6. The forked type dental hygiene tool of claim 4 wherein said bristle brush means have a cone shaped working surface.

7. The forked type dental hygiene tool of claim 4 wherein said fixing means are projections on a surface of said handle means co-operating interdigitally to prevent any sliding motion.

* * * * *